(12) United States Patent
Nelson (10) Patent No.: US 9,585,574 B2
(45) Date of Patent: Mar. 7, 2017

(54) MAGNETIC RESONANCE SYSTEM AND METHOD INCLUDING AN AUTOMATED NON-MAGNETIC MEDICAL MONITOR

(75) Inventor: Mark Nelson, Satellite Beach, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1665 days.

(21) Appl. No.: 12/918,820

(22) PCT Filed: Feb. 2, 2009

(86) PCT No.: PCT/IB2009/050418
§ 371 (c)(1),
(2), (4) Date: Aug. 23, 2010

(87) PCT Pub. No.: WO2009/107008
PCT Pub. Date: Sep. 3, 2009

(65) Prior Publication Data
US 2010/0331667 A1 Dec. 30, 2010

Related U.S. Application Data (60) Provisional application No. 61/032,082, filed on Feb. 28, 2008.

(51) Int. Cl.
*A61B 5/055* (2006.01)
*A61B 5/022* (2006.01)
*A61B 5/021* (2006.01)
*G01R 33/28* (2006.01)

(52) U.S. Cl.
CPC .......... *A61B 5/022* (2013.01); *A61B 5/02141* (2013.01); *A61B 5/055* (2013.01); *G01R 33/288* (2013.01)

(58) Field of Classification Search
CPC ..... A61B 5/02141; A61B 5/022; A61B 5/055; G01R 33/288
See application file for complete search history.

(56) References Cited

U.S. PATENT DOCUMENTS

| | | | | |
|---|---|---|---|---|
| 5,267,589 A | * | 12/1993 | Watanabe | 137/625.65 |
| 5,323,776 A | | 6/1994 | Blakeley et al. | |
| 5,394,873 A | | 3/1995 | Kraemer et al. | |
| 5,445,162 A | * | 8/1995 | Ives | 600/544 |
| 5,464,014 A | * | 11/1995 | Sugahara | 600/411 |
| 5,590,653 A | * | 1/1997 | Aida et al. | 600/411 |
| 5,798,600 A | | 8/1998 | Sager et al. | |

(Continued)

FOREIGN PATENT DOCUMENTS

| | | |
|---|---|---|
| JP | H06269426 A | 9/1994 |
| WO | 0209812 A1 | 2/2002 |
| WO | 2007082495 A1 | 7/2007 |

*Primary Examiner* — Ruth S Smith (57) ABSTRACT

In magnetic resonance imaging (MRI), the powerful magnetic fields can interfere with, damage, cause premature failure in, and attract certain non-MR safe instruments. Electromagnetic ally sensitive components are eliminated in favor of MR safe components, such as ceramic piezoelectric components and bi-metallic components. Instruments that previously had to be kept a safe distance away from the main magnet (12), e.g., beyond the 5 Gauss line, while a patient was being scanned are now allowed near the patient without fear of damage to the instrument (40) or danger to the patient and medical staff or the MRI device (10).

11 Claims, 5 Drawing Sheets (56) References Cited

U.S. PATENT DOCUMENTS

| | | |
|---|---|---|
| 6,102,678 A | 8/2000 | Peclat |
| 6,164,933 A | 12/2000 | Tani et al. |
| 6,557,558 B1 | 5/2003 | Tajima et al. |
| 2002/0120190 A1 | 8/2002 | Chang |
| 2003/0225328 A1 | 12/2003 | DeMeester et al. |
| 2004/0267111 A1* | 12/2004 | Feinberg ................. 600/411 |
| 2005/0244972 A1* | 11/2005 | Hilson et al. ............. 436/47 |
| 2006/0079758 A1 | 4/2006 | Susi |
| 2006/0184008 A1* | 8/2006 | Zatezalo et al. .......... 600/420 |
| 2006/0293601 A1* | 12/2006 | Lane et al. ............... 600/495 |
| 2007/0093718 A1 | 4/2007 | Lane et al. |
| 2007/0112274 A1* | 5/2007 | Heitzmann et al. ....... 600/485 |
| 2008/0183398 A1* | 7/2008 | Petrucelli ................. 702/19 |
| 2009/0105581 A1* | 4/2009 | Widenhorn ............... 600/411 |
| 2010/0099975 A1* | 4/2010 | Faro et al. ................ 600/411 |
| 2010/0137725 A1* | 6/2010 | Takahashi et al. ........ 600/493 |

* cited by examiner

MAGNETIC RESONANCE SYSTEM AND METHOD INCLUDING AN AUTOMATED NON-MAGNETIC MEDICAL MONITOR

CROSS REFERENCE TO RELATED APPLICATIONS

This application claims the benefit of U.S. provisional application ser. no. 61/032,082 filed Feb. 28, 2008, which is incorporated herein by reference.

The present application relates to the diagnostic imaging arts. It finds particular application in accessories safe for use in the presence of a magnetic resonance imaging scanner that produces a strong magnetic field, and will be described with particular reference thereto. It is to be appreciated, however, that the present application can also be used in more traditional settings in the absence of strong magnetic fields and is not limited to the aforementioned application.

Conventional magnetic resonance imaging (MRI) uses powerful magnetic fields to align dipoles in a subject in an imaging region. Often, the suites that house the MRI magnets are magnetically shielded to prevent the powerful magnetic fields from interfering with other magnetically sensitive devices. One potentially dangerous side effect of such a powerful magnetic field is the physical attraction it exerts on nearby ferromagnetic material. If a metal object is brought within close proximity to the magnet, the object can be propelled with great velocity toward the magnet risking harm to people in the vicinity, the magnet, and the object itself. Thus, metal objects or objects with metal components must be kept at a safe distance away from the magnet when it is operating at field. Even if the magnetic attraction is not powerful enough to physically displace the device as a whole, the field can still exert forces and torques that would affect the operation of the device.

Another side effect is that the magnetic field can damage magnetically sensitive instruments and cause them to prematurely fail. Even at distances where physical attraction is not a danger, some magnetic field exists and can affect sensitive components. This may be a temporary failure, and once removed from the field the device operates normally, but permanent damage can be caused, such as with deformation of permanent magnets leading to permanent failure. The magnetic forces on moving electromagnetic or ferrous parts can cause extra loading leading to premature failure.

Automatic blood pressure monitors, for example, contain pumps that are typically driven by non-MRI safe components. Automated non-invasive blood pressure devices and gas monitors currently use centrifugal or peristaltic pumps driven by electromagnetic motors. Valves operating in these devices are actuated by electromagnetic solenoids. In order to be safe, these monitors must be kept some safe distance away from the magnet. If blood pressure monitoring is desired of a patient within the MRI device, long tubes or hoses are be run from the pump and valve portions of the monitor to the patient mounted cuff, mask, or other sensor, presenting a physical obstacle for the patient and medical personnel to deal with. The hoses negatively impact efficient workflow as the monitor and patient are maneuvered around the MRI suite. Additionally, the components within the monitor are still in the MR suite and affected by the magnetic field, and tend to fail prematurely. In the past, devices have been assigned "MR Conditional" ratings where devices are labeled with the maximum magnetic field exposure allowable. This can be translated into a safe distance from an MRI machine with a constant $B_0$ field.

To protect sensitive components from the magnetic field, ferromagnetic shields are sometimes used. While these shields help protect components from damage, they are not completely magnetic field impenetrable and they present the added risk of physical attraction so must be kept a safe distance away. While a shield can help alleviate premature failure of sensitive components, long hoses still must be run from the patient in the MRI device to the monitor.

The present application provides a new and improved MRI safe device, which overcomes the above-referenced problems and others.

In accordance with one aspect, a magnetic resonance system is provided. A main magnet generates a substantially uniform main magnetic field in an imaging region. A gradient coil assembly imposes gradient magnetic fields on the main magnetic field, spatially encoding the main magnetic field. A radio frequency assembly induces magnetic resonance in selected dipoles of a subject in the imaging region, and receives magnetic resonance signals from the imaging region. An automated non-magnetic monitor measures and displays a parameter of the subject.

In accordance with another aspect, an MRI safe blood pressure monitor is provided. A pressure cuff applies pressure to an artery of a patient. A first transducer senses audible events within the artery under pressure. A piezoelectric ceramic peristaltic pump pressurizes the pressure cuff. A first high voltage driver drives the piezoelectric pump. A second transducer senses the pressure applied to the pressure cuff. A first piezoelectric ceramic diaphragm valve releases pressure from the pressure cuff at a controlled, linear rate. A second high voltage driver drives the first piezoelectric diaphragm valve. Pneumatic connections connect at least the pump and the pressure cuff. Control circuitry controls at least the pump and the diaphragm valve. A power supply provides power to at least the first and second high voltage drivers.

In accordance with another aspect, a method of taking the blood pressure of a subject in a magnetic field is provided. A main magnetic field is generated with a main magnet of a magnetic resonance imaging device. A pressure cuff located in the main magnetic field is inflated by closing a first, linear piezoelectric ceramic diaphragm valve, closing a second, piezoelectric ceramic diaphragm dump valve, and actuating a piezoelectric ceramic pump. A pressure is read by releasing air from the pressure cuff by opening the first valve and turning the pump off. After a pressure reading is taken, the remaining air is released from the cuff by opening the second valve.

One advantage lies in the ability to monitor a patient's blood pressure in a high magnetic field environment without the use of long hoses.

Another advantage lies in the ability to monitor administered gases in a high magnetic field environment without the use of long hoses, where a piezoelectric ceramic pump draws the vacuum required to sample gases.

Another advantage lies in increased component life in high magnetic field environments.

Another advantage lies in increased mobility and patient access.

Another advantage lies in the reduction of ferromagnetic material in the vicinity of the MRI device.

Another advantage lies in increased safety for the patient and medical staff.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
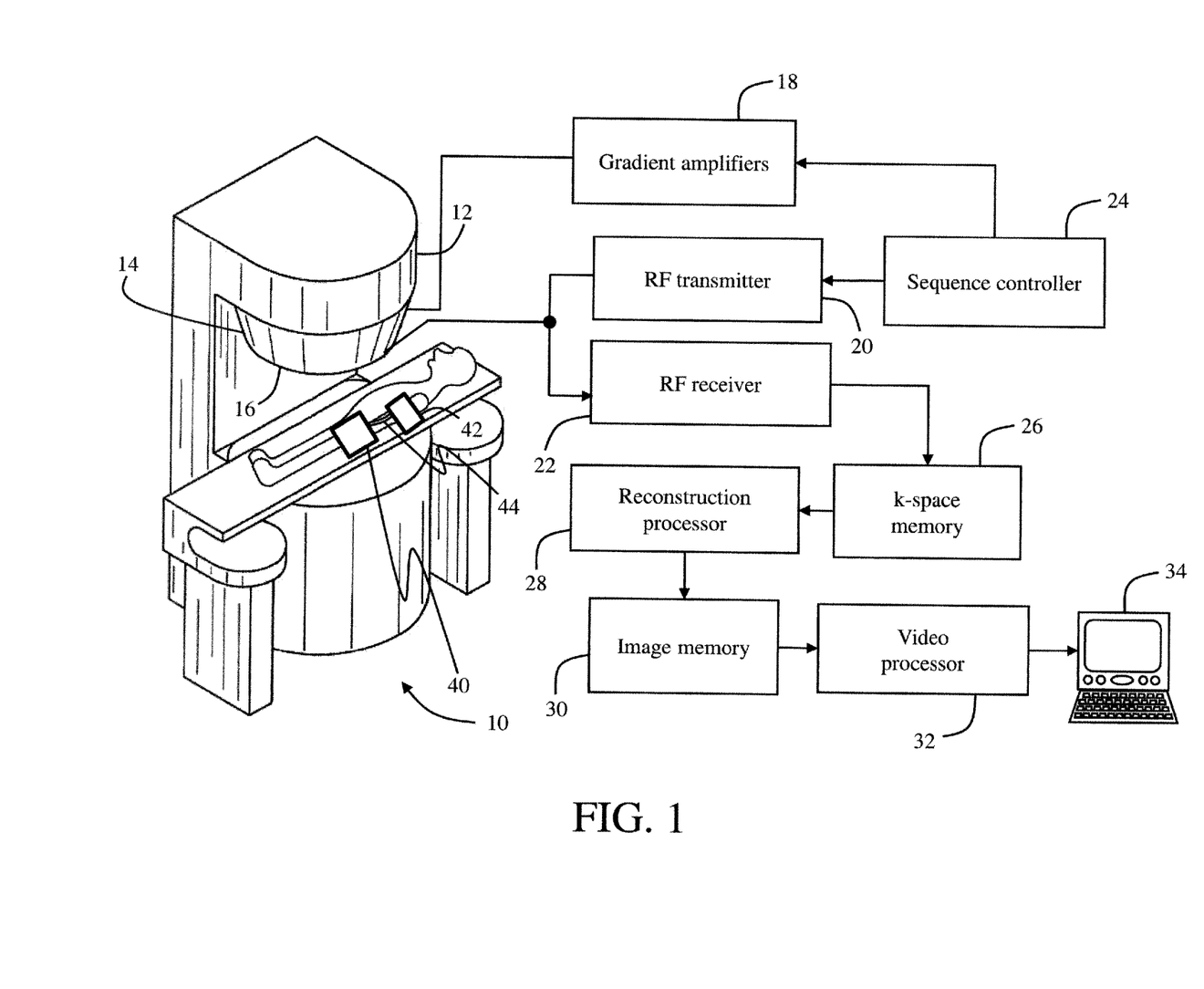
FIG. 1 is a diagrammatic illustration of a magnetic resonance imaging apparatus with an MR safe medical monitor.

With reference to FIG. 1, a magnetic resonance scanner 10 is depicted. The magnetic resonance scanner 10 can be an open field system that includes a vertical main magnet assembly 12. The main magnet assembly 12 produces a substantially constant main magnetic field oriented along a vertical axis of an imaging region. Although a vertical main magnet assembly 12 is illustrated in part to aid visualization, it is to be understood that other magnet arrangements, such as cylindrical, and other configurations are also contemplated. The main magnet 12 in an open system may have a field strength of around 2500 Gauss (0.25 T) to 10,000 Gauss (1.0 T). A bore type system may generate magnetic fields of 15,000 Gauss (1.5 T) to 70,000 Gauss (7.0 T) or more. The 5 Gauss line is typically closer at lower field strengths and further at high field strengths, but can also vary with other factors such as shielding and configuration.

A gradient coil assembly 14 produces magnetic field gradients in the imaging region for spatially encoding the main magnetic field. Preferably, the magnetic field gradient coil assembly 14 includes coil segments configured to produce magnetic field gradient pulses in three orthogonal directions, typically longitudinal or z, transverse or x, and vertical or y directions.

A radio frequency coil assembly 16 generates radio frequency pulses for exciting resonance in dipoles of the subject. The radio frequency coil assembly 16 also serves to detect resonance signals emanating from the imaging region. The radio frequency coil assembly 16 is a send/receive coil that images the entire imaging region, however, local send/receive coils or local dedicated receive coils are also contemplated.

Gradient pulse amplifiers 18 deliver controlled electrical currents to the magnetic field gradient assembly 14 to produce selected magnetic field gradients. A radio frequency transmitter 20, preferably digital, applies radio frequency pulses or pulse packets to the radio frequency coil assembly 16 to excite selected resonance. A radio frequency receiver 22 is coupled to the coil assembly 16 or separate receive coils to receive and demodulate the induced resonance signals.

To acquire resonance imaging data of a subject, the subject is placed inside the imaging region. A sequence controller 24 communicates with the gradient amplifiers 18 and the radio frequency transmitter 20 to supplement the optical manipulation of the region of interest. The sequence controller 24, for example, produces selected repeated echo steady-state, or other resonance sequences, spatially encode such resonances, selectively manipulate or spoil resonances, or otherwise generate selected magnetic resonance signals characteristic of the subject. The generated resonance signals are detected by the RF coil assembly 16 or local coil (not shown), communicated to the radio frequency receiver 22, demodulated, and stored in a k-space memory 26. The imaging data is reconstructed by a reconstruction processor 28 to produce one or more image representations that are stored in an image memory 30. In one suitable embodiment, the reconstruction processor 28 performs an inverse Fourier transform reconstruction.

The resultant image representation(s) is processed by a video processor 32 and displayed on a user interface 34 equipped with a human readable display. The interface 34 is preferably a personal computer or workstation. Rather than producing a video image, the image representation can be processed by a printer driver and printed, transmitted over a computer network or the Internet, or the like. Preferably, the user interface 34 also allows a radiologist or other operator to communicate with the sequence controller 24 to select magnetic resonance imaging sequences, modify imaging sequences, execute imaging sequences, and so forth.

A portable monitor 40 is located with the patient in the magnetic field. The monitor 40 in the illustrated embodiment is a blood pressure monitor, and is connected to a typical pressure cuff 42 by at least one air hose 44. A dual hose system is described below. It is to be understood, however, that any parameter can be measured, and the present application is not necessarily limited specifically to blood pressure monitors. When measuring a blood pressure, the cuff 42 is inflated exerting a measurable pressure on the patient, typically the bicep of the patient. The cuff 42 is inflated so that the pressure of the cuff 42 is increased to a pressure above the arterial systolic pressure of the patient. This temporarily stops blood flow through the brachial artery. Air is then allowed to bleed out of the cuff at a constant rate. When blood begins to flow in the brachial artery, that is, when the cuff 42 or other sensor on the arm detects a pulse, the monitor 40 records the pressure value as the patient's systolic pressure. Air continues to bleed from the cuff 42 until the cuff can no longer detect the pulse, and the pressure value at which the pulse is lost is recorded as the patient's diastolic pressure.

Figure 2:
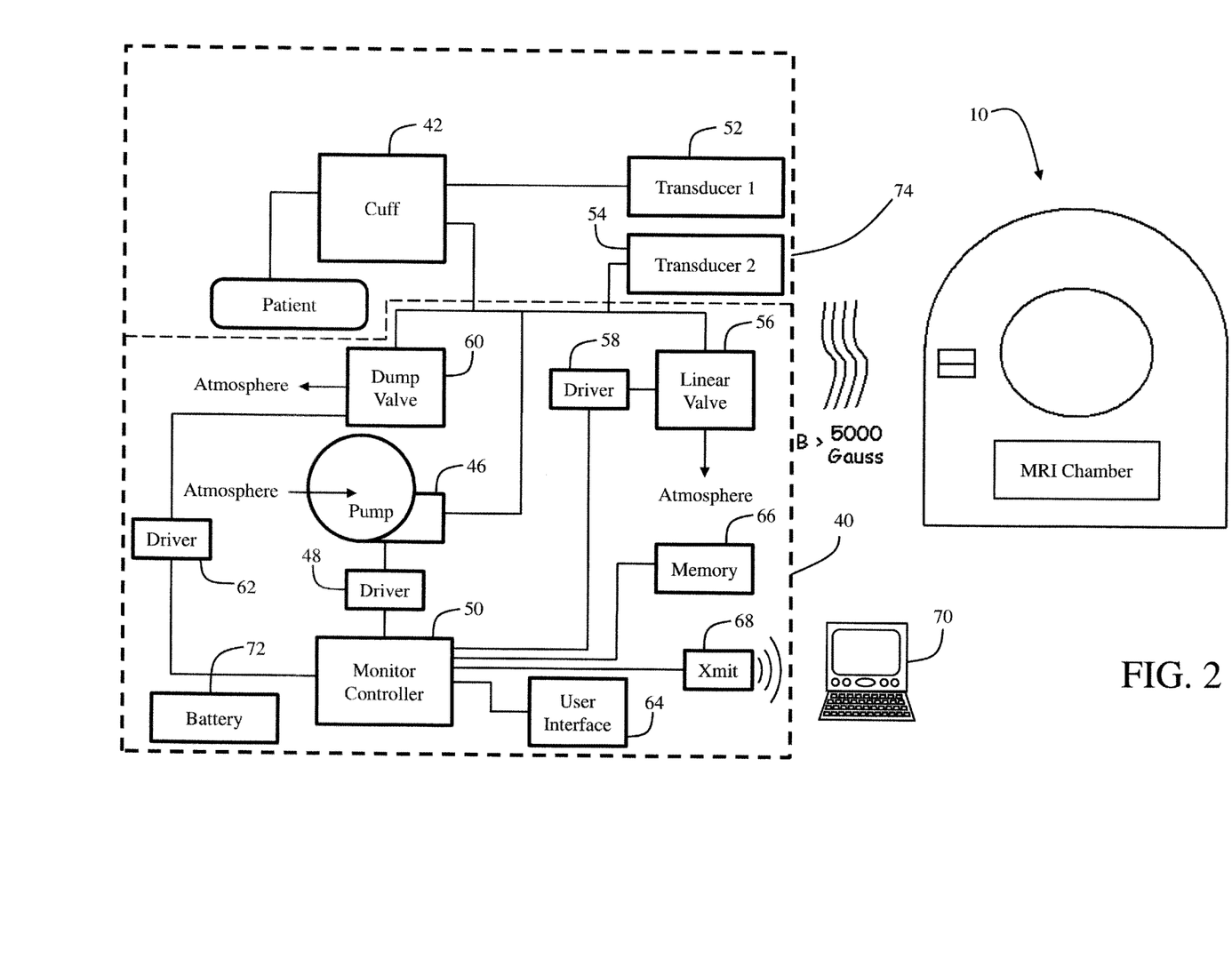
FIG. 2 is a diagrammatic illustration of a blood pressure monitor, in accordance with the present application.
Figure 3:
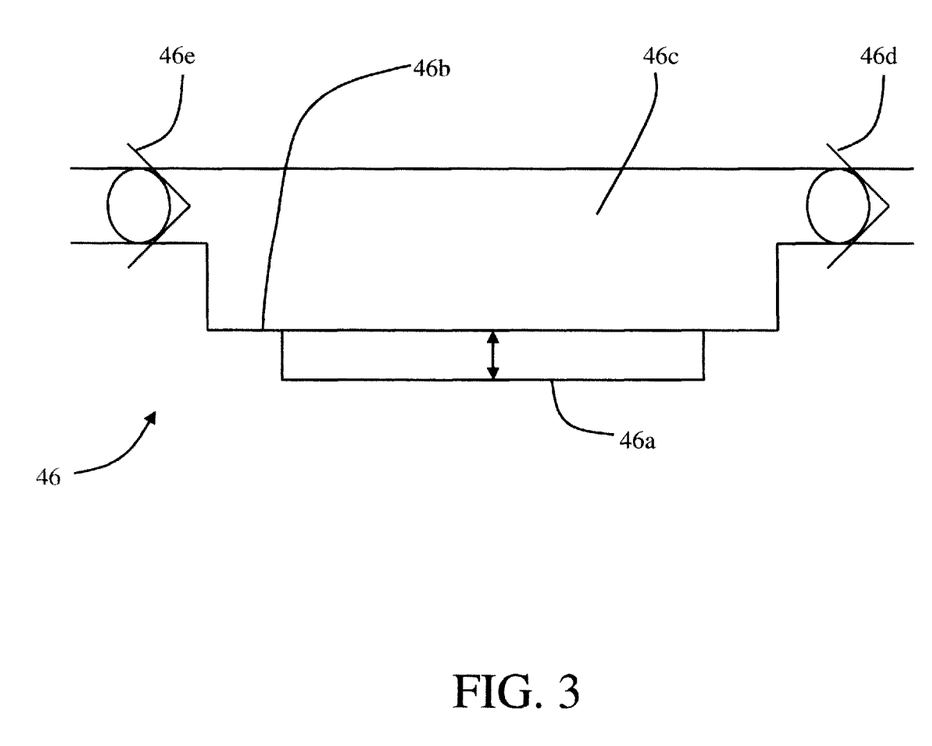
FIG. 3 is illustrative of a valve for the MR safe medical monitor.

With reference to FIG. 2, the blood pressure monitor 40 is shown in more detail, including components that make the above-described measurements possible. In order to increase the pressure in the cuff 42 a pump 46 draws air from the atmosphere and pumps it to the cuff 42. As the cuff 42 inflates the system is closed so that pressure increases within the cuff 42. In an embodiment illustrated in FIG. 3, the pump 46 is a piezoelectric pump, and more specifically, a peristaltic piezoelectric ceramic-actuated pump, although other types of piezoelectric pumps are also contemplated. A piezoelectric element 46a expands and contracts in the direction indicated by the arrow. As the piezoelectric element is actuated, it deflects a flexible diaphragm 46b. As the diaphragm 46b deflects, it reduces the volume of a pump chamber 46c, pumping fluid from the chamber via an exit check valve 46d. As the piezoelectric element 46a relaxes, the volume of the pump chamber 46c increases and draws fluid in through an entry check valve 46e. Both check valves 46d, 46e are pressure-actuated one way valves preventing reverse flow through the pump chamber 46c. The piezoelectric element 46a of the pump 46 is driven by an associated high voltage driver 48. The driver 48 is controlled by a monitor controller 50.

Figure 4:
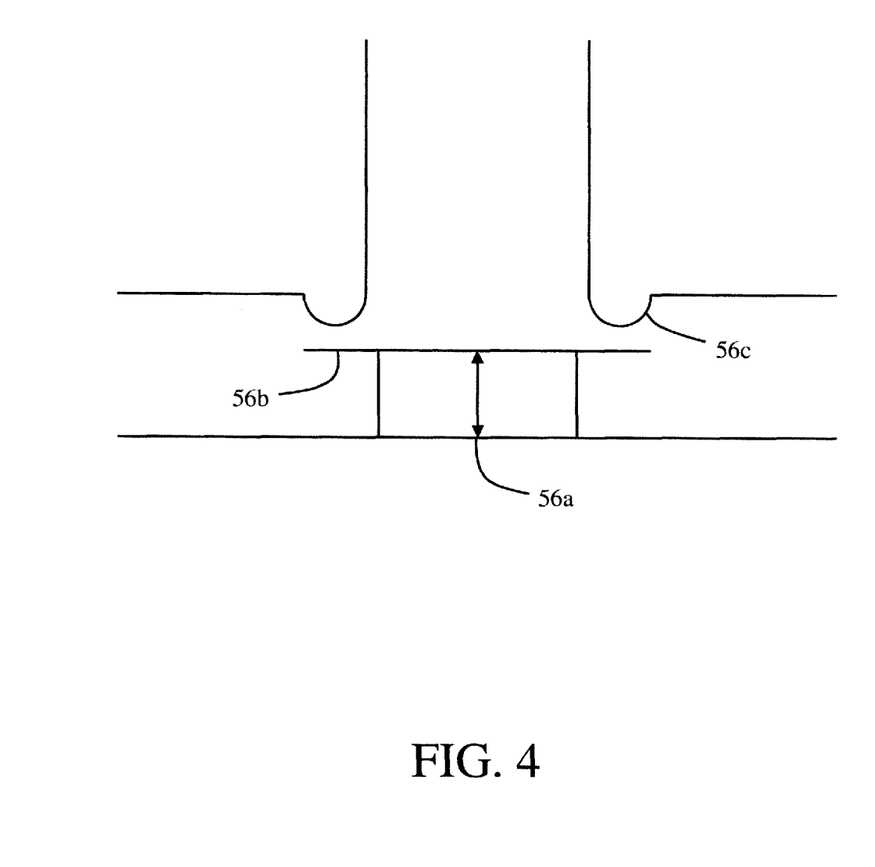
FIG. 4 is illustrative of a pump for the MR safe monitor.

In order to sense whether blood is flowing in the brachial artery, a first transducer 52 is located in or adjacent the cuff 42. When blood begins to flow, it is accompanied by a characteristic sound (the first Korotkoff sound) that is produced by turbulent blood flow and detected by the transducer 52. A second transducer 54 measures the pressure of the cuff 42. After the pump 46 inflates the cuff 42 to pressure, air is bled from the cuff 42 via a linear valve 56. In an embodiment illustrated in FIG. 4, the linear valve 56 is a piezoelectric ceramic diaphragm valve. a piezoelectric element 56a expands and contracts as indicated by the arrows. As the piezoelectric element expands, it forces a valve element 56b to come into contact with a valve seat 56c sealing the valve 56. When the piezoelectric element 56a relaxes, the valve 56 opens and fluid can flow therethrough. Optionally, a pilot operated piezoelectric valve can be used. The linear valve 56 has its own associated high voltage driver 58 that is also controlled by the monitor controller 50. Optionally, the linear valve can be driven by a bi-metallic element 56a, where measured electrical current creates heat and causes a known deflection. The valve then allows a known flow rate to pass. This type is also non-magnetic, but would not require the additional high-voltage driver When the pressure of the cuff 42 is between the patient's systolic and diastolic pressures, blood flow will be turbulent as the arterial pressure jumps above the cuff pressure and falls back below the cuff pressure with the beating of the patient's heart. As long as the pressure of the cuff 42 is between the systolic and diastolic pressures, the first transducer 52 can detect the turbulent blood flow. Once the cuff pressure drops below the systolic pressure, flow through the brachial artery is no longer turbulent, as the artery is no longer constricted. No further sounds are detected. When the first transducer 52 no longer detects any sounds, the pressure reported by the second transducer 54 at which this occurs is recorded as the diastolic pressure.

Once the diastolic pressure has been recorded, a dump valve 60 opens to release the remaining air in the cuff 42 to the atmosphere. In one embodiment, like the linear valve 56, the dump valve 60 is a piezoelectric ceramic diaphragm valve. Similarly, the dump valve 60 is driven by its own high voltage driver 62. The drivers 48, 58, 62 are all controlled to perform the above-detailed process by the monitor controller 50. During inflation of the cuff 42, the pump 46 is turned on and both the linear valve 56 and the dump valve 60 are closed. During blood pressure measurement, the pump 46 is turned off, the linear valve 56 is opened, and the dump valve 60 remains closed. Once the diastolic pressure has been read, and during periods of non-use, the pump 46 is off, and both valves 56, 60 are opened. If the monitor 40 fails to achieve a reading, the controller 50 can immediately start the process again. Optionally, the dump valve can be driven by a bi-metallic element that converts electricity to heat to movement and valve actuation, without need for an additional high-voltage driver.

As mentioned previously, the process is controlled by the monitor controller 50. Preferably, a user can interface with the monitor controller 50 with a user interface 64. The user can order a reading now, or set periodic readings, and review recent pressure readings stored in a monitor memory 66. Optionally, a wireless transceiver 68 is included in the monitor 40 so that the controller 50 can transmit readings to a remote workstation, such as an in-suite, operator's, or nurse's station, or monitor processing unit 70. A suitable power supply 72 such as a battery, an AC adapter, or a system that draws power from the MR system provides power to the monitor 40. Preferably, the monitor 40 is equipped with a rechargeable battery, such as a non-magnetic lithium ion battery, that can be plugged into a wall socket when idle, but cordless when in use.

By using ceramic piezoelectric elements, electromagnetically sensitive components are absent from the monitor 40. Thus, it can be given an "MR Safe" rating and accompany the patient in the field of the MR device 10 eliminating the need for extensive cables and tubes leading from the monitor 40 to the patient. The piezoelectric design is equally applicable to wireless, portable, tabletop, and pedestal mounted blood pressure monitors alike, but specifically for monitors that can travel with the patient into the bore of an MR device. Optionally, the monitor is shielded with an electromagnetic interference shield 74 to prevent the monitor 40 from negatively impacting image acquisition or quality. Further, the monitor controller 50 and the memory 66 are shielded from the magnetic fields.

In another embodiment, a gas monitor, such as one that measures end-tidal $CO_2$, or delivers anesthetic gases, is configured with piezoelectric ceramic pumps and valves for use in MRI systems. In gas monitors, a breathing mask is placed over the patient's mouth. A piezoelectric peristaltic pump pumps gas from the mask or an associated exhaust line. Piezoelectric valves are operated to move a metered volume of exhaust gas into an analysis chamber, hold the gas in the chamber for the analysis duration, and exhaust the gas after analysis.

Figure 5:
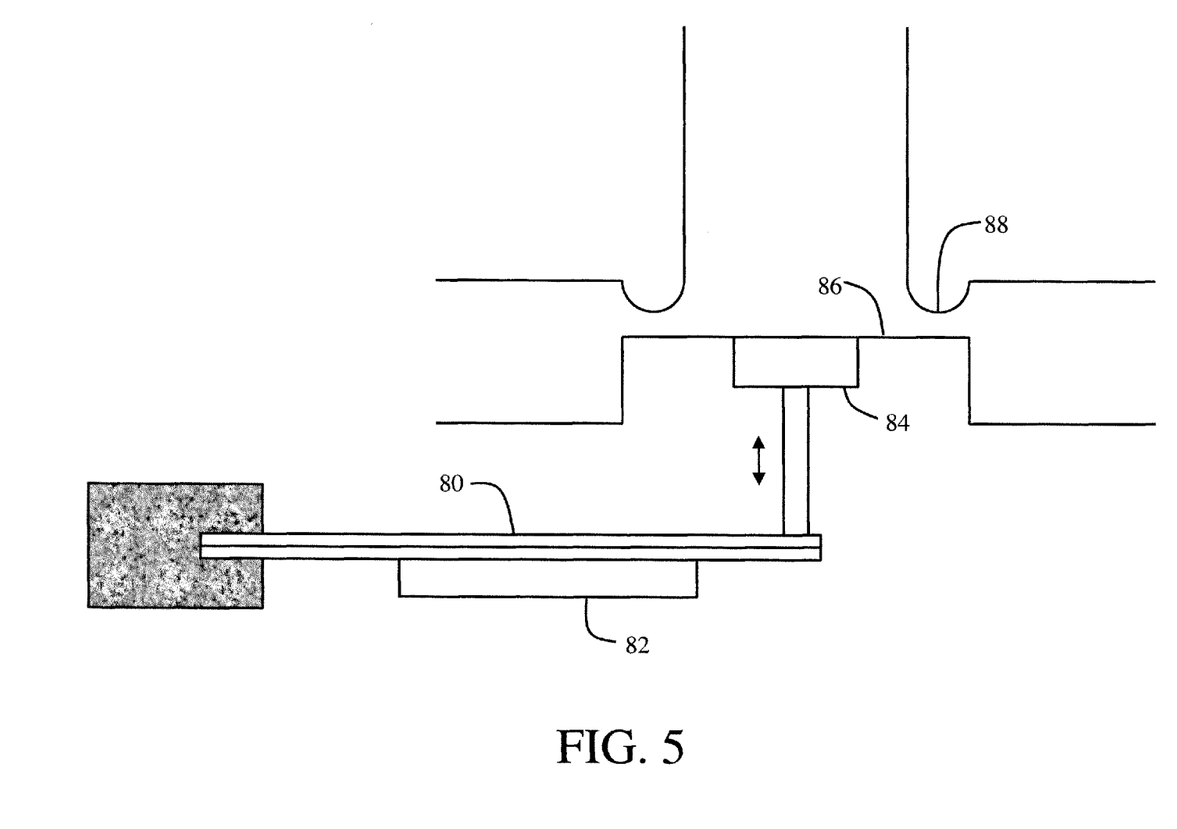
FIG. 5 is an alternate embodiment of an MR safe valve.

Other types of magnetic field safe pumps and valves are also contemplated. As illustrated in FIG. 5, a bimetallic element 80 is heated by a heater 82 and allowed to cool to cause it to move a plunger 84 in the direction indicated by the arrows. The plunger 84 flexes a diaphragm 86 and causes it to actuate a valve seat 88 between open and closed positions. Analogously, alternate heating and cooling of the bimetallic element 80 can pump the diaphragm of a peristaltic pump. Other types of MR safe valves and pumps are also contemplated.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A magnetic resonance system comprising:
 a main magnet for generating a substantially uniform main magnetic field in an examination region;
 a gradient coil assembly for imposing gradient magnetic fields on the main magnetic field in the examination region, spatially encoding the main magnetic field;
 a radio frequency assembly for inducing magnetic resonance in selected dipoles of a subject in the examination region, and receiving the magnetic resonance; and
 an automated non-magnetic monitor disposed in the examination region to measure at least one physiological parameter of the subject, the non-magnetic monitor including one of a blood pressure monitor and a gas analysis monitor, wherein the non-magnetic monitor further includes an electrically operated pump disposed in the main magnetic field.

2. The magnetic resonance system of claim 1 wherein the pump includes a piezoelectric ceramic peristaltic pump.

3. The magnetic resonance system as set forth in claim 2, further including:
 a high voltage driver for the piezoelectric pump disposed in the examination region.

4. The magnetic resonance system as set forth in claim 1, wherein the monitor includes at least one valve disposed in the main magnetic field.

5. The magnetic resonance system as set forth in claim 4, wherein the at least one valve includes:
 a piezoelectric ceramic diaphragm valve; and a high voltage driver for the piezoelectric diaphragm valve.

6. The magnetic resonance system as set forth in claim 1, wherein the monitor includes a blood pressure monitor, the blood pressure monitor further including:
   at least one valve disposed in the main magnetic field;
   a controller for controlling high voltage drivers for driving the pump and the at least one valve;
   a memory for storing at least blood pressure readings and a time at which they were taken;
   an electromagnetically compatible enclosure around the controller and the memory to shield from radiate emissions.

7. The magnetic resonance system as set forth in claim 1, wherein the main magnet generates a magnetic field of at least 2500 Gauss (0.25 T) in the examination region.

8. A method of magnetic resonance comprising:
   generating a main magnetic field with a main magnet of at least 2500 Gauss of a magnetic resonance imaging device;
   applying gradient magnetic fields to the examination region with a gradient coil system;
   applying RF pulses to the examination region with an RF assembly;
   controlling at least one valve and at least one pump located in the at least 2500 Gauss main magnetic field to alternately inflate and deflate a blood pressure cuff.

9. The method as set forth in claim 8, further including:
   inflating a pressure cuff located in the main magnetic field by closing a first, linear piezoelectric ceramic diaphragm valve, closing a second, piezoelectric ceramic diaphragm dump valve, and actuating a piezoelectric ceramic pump;
   reading a pressure by releasing air from the pressure cuff by opening the first valve and turning the pump off; and
   releasing remaining air from the cuff by opening the second valve.

10. The method as set forth in claim 9 wherein the main magnetic field is greater than or equal to 5000 Gauss.

11. The method as set forth in claim 8, further including: wirelessly transmitting a blood pressure measurement to a remote location.

* * * * *